(12) United States Patent
Alsters

(10) Patent No.: US 9,302,972 B2
(45) Date of Patent: Apr. 5, 2016

(54) PROCESS FOR THE PREPARATION OF AZELEIC ACID FROM 9-OCTADECENEDIOIC ACID

(71) Applicant: Paulus Lamburtus Alsters, Echt (NL)

(72) Inventor: Paulus Lamburtus Alsters, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/366,051

(22) PCT Filed: Dec. 12, 2012

(86) PCT No.: PCT/EP2012/075273
§ 371 (c)(1),
(2) Date: Jun. 17, 2014

(87) PCT Pub. No.: WO2013/092353
PCT Pub. Date: Jun. 27, 2013

(65) Prior Publication Data
US 2015/0183704 A1    Jul. 2, 2015

(30) Foreign Application Priority Data
Dec. 20, 2011 (EP) ............ 11194564

(51) Int. Cl.
| C07C 51/285 | (2006.01) |
| C07C 67/333 | (2006.01) |
| C07C 55/18  | (2006.01) |
| C08G 69/00  | (2006.01) |

(52) U.S. Cl.
CPC ........... *C07C 51/285* (2013.01); *C07C 55/18* (2013.01); *C07C 67/333* (2013.01); *C08G 69/00* (2013.01)

(58) Field of Classification Search
CPC ........ C07C 57/13; C07C 55/18; C07C 69/48; C07C 51/285; C07C 69/00
See application file for complete search history.

(56) References Cited

U.S. PATENT DOCUMENTS

| 5,002,988 A * | 3/1991 | Ono et al. ............ 524/1 |
| 5,962,285 A * | 10/1999 | Anderson et al. ........ 435/142 |
| 2013/0131379 A1* | 5/2013 | Lemaire .......... C07C 51/29 562/525 |

FOREIGN PATENT DOCUMENTS

| EP | 1 053 992 | 11/2000 |
| FR | 2 957 074 | 9/2011 |
| FR | WO 2011/107721 | * 9/2011 |
| GB | 1 224 144 | 3/1971 |
| IT | WO94/10122 | * 5/1994 |
| WO | WO 95/00243 | 1/1995 |

OTHER PUBLICATIONS

International Search Report for PCT/EP2012/075273, mailed Mar. 15, 2013.

* cited by examiner

*Primary Examiner* — Gregory Listvoyb
(74) *Attorney, Agent, or Firm* — Nixon & Vanderhye P.C.

(57) ABSTRACT

The invention relates to a process for the preparation of azelaic acid or alkyl azelate starting from mono-unsaturated 9-octadecenedioic acid or its corresponding alkylester characterized in that the process comprises at least the following step: •reacting the mono-unsaturated 9-octadecene dioic acid or its corresponding alkylester with hydrogen peroxide in the presence of an organic carboxylic acid other than 9-octadecene dioic acid and a suitable catalyst to effect cleavage of the double bond in the mono-unsaturated 9-octadecene dioic acid or its corresponding alkylester. The invention further relates to the azelaic acid or alkyl azelate obtainable by the process according to the invention and to the use of azelaic acid or alkyl azelate or monomers derived there from for the preparation of a polymer, especially a polyamide.

9 Claims, No Drawings

PROCESS FOR THE PREPARATION OF AZELEIC ACID FROM 9-OCTADECENEDIOIC ACID

This application is the U.S. national phase of International Application No. PCT/EP2012/075273 filed 12 Dec. 2012 which designated the U.S. and claims priority to EP Patent Application No. 11194564.8 filed 20 Dec. 2011, the entire contents of each of which are hereby incorporated by reference.

The present invention relates to a process for the preparation of nonanedioic acid (azelaic acid) or alkyl ester derivatives thereof (alkyl azelates) starting from mono-unsaturated 9-octadecenedioic acid or its corresponding alkylester. The invention further relates to the compounds obtainable by the process and to their use, specifically their use in the preparation of a polymer.

A process for the preparation of pelargonic acid and azelaic acid starting from 9-octadecenoic acid (oleic acid) is known from an article by Antonelli et al in J. Org. Chem. 1998, 63, 7190-7206. In this article, the one step oxidative cleavage of alkenes to carboxylic acids in the presence of aqueous hydrogen peroxide and methyltrioctyl-ammonium tetrakis(oxodiperoxotungsto)phosphate as the catalyst is described. One of the alkenes used is oleic acid. From oleic acid, pelargonic and azelaic acid are obtained in a yield of respectively 82 and 79% according to the described methodology. Since the stoichiometry of the oxidative cleavage requires 4 molar equivalents hydrogen peroxide, whereas oleic acid generates only 1 molar equivalent of azelaic acid on cleavage, production of azelaic acid from oleic acid by hydrogen peroxide based oxidative cleavage is industrially not very attractive. Industrially, azelaic acid is therefore produced via ozonolysis of oleic acid followed by dioxygen oxidation, as described by Cornils and Lappe in "Dicarboxylic Acids, Aliphatic; Ullmann's Encyclopedia of Industrial Chemistry", Wiley (2010). Still, this route suffers from relatively high oxidant costs and from only 50% carbon efficiency. With carbon efficiency is meant here and hereinafter the percentage of carbon atoms from the starting compound that is found in the desired products.

From the point of view of using the obtained products as starting point for the further synthesis of various compounds such as for example polymers, it would be very advantageous to be able to produce azelaic acid in high yield without producing the mono-functional acid pelargonic acid in considerable amounts. Since for the production of polymers two functional groups are necessary to build a polymer chain, mono-functional compounds cannot be used to that end. Even more so, mono-functional compounds present in a monomer mixture that is to be used in a polymerization should be removed as the presence of even a small amount of a mono-functional compound will negatively influence the polymer properties such as for example the molecular weight of the polymer obtained. Therefore there exists a need for a process for the production of azelaic acid in high yields while minimizing the amount of by-products, especially mono-functional by-products. This can be achieved via the oxidative cleavage of 9-octadecenedioic acid or its corresponding alkylester, since these starting materials yield 2 mol equivalents of azelaic acid or alkyl derivatives thereof on oxidative cleavage of the alkene double bond. From an industrial manufacture point of view, it would be highly advantageous if oxidative cleavage of 9-octadecenedioic acid or its corresponding alkylester can be done in one step with aqueous hydrogen peroxide as the oxidant. The article by Antonelli doesn't describe the use of 9-octadecenedioic acid as a starting material.

It has now been found that azelaic acid or alkyl azelate can be prepared with very high yields in a process starting from 9-octadecenedioic acid or its corresponding alkylester. With alkyl ester derivatives are meant both mono- and dialkyl ester derivatives, either pure or as a mixtures. The process for the preparation of azelaic acid or alkyl azelate starting from 9-octadecenedioic acid or its corresponding alkylester comprises at least the following step:

reacting 9-octadecenedioic acid or its corresponding alkylester with aqueous hydrogen peroxide in the presence of an organic carboxylic acid other than 9-octadecene dioic acid and a suitable catalyst to effect cleavage of the double bond in 9-octadecenedioic acid or the corresponding alkylester.

The desired azelaic acid or alkyl azelate can be obtained in high yields with this process. Using an in situ generated catalyst system from methyltrioctylammonium chloride, phosphoric acid, tungstic acid, and hydrogen peroxide instead of isolated methyltrioctylammonium tetrakis(oxodiperoxotungsto)phosphate as the catalyst, it was found that the process as described in the Antonelli publication when applied to the dimethyl ester of 9-octadecenedioic acid, did not generate azelaic acid. Instead, only the epoxide derived from the dimethyl ester of 9-octadecenedioic acid was obtained.

To check whether this unexpected lack of oxidative cleavage observed with the dimethyl ester of 9-octadecenedioic acid was due to the use of an in situ generated catalyst rather than an isolated peroxotungstate catalyst, the oxidative cleavage of (E)-2-octene was attempted under exactly the same conditions and using the same reaction equipment as for the attempted cleavage of the dimethyl ester of 9-octadecenedioic acid. Clean formation of a mixture of acetic acid and hexanoic acid at full conversion was observed for (E)-2-octene, indicating that the lack of oxidative cleavage for the dimethyl ester of 9-octadecenedioic acid is caused by the nature of the substrate and not by a switch from an isolated peroxotungstate catalyst to an in situ generated catalyst.

After careful research it was found that the presence of an organic carboxylic acid additive besides the substrate in the reaction mixture was necessary for an efficient oxidative cleavage towards the desired azelaic acid or alkyl azelate. It was found to be advantageous to add the organic carboxylic acid as early in the process as possible, preferably the organic carboxylic acid is present at the start of the reaction. The organic carboxylic acid can be added separately to the reactor or it can be combined with the mono-unsaturated 9-octadecenedioic acid or an alkyl ester derivative thereof and fed to the reactor together with it.

Examples of suitable organic carboxylic acids are mono- or dicarboxylic acids with 1-12 carbon atoms. The mono- or dicarboxylic acid used in the reaction should be sufficiently soluble in the reaction medium at the oxidative cleavage temperature. Preferably the acid dissolves for at least 80%, more preferably for at least 90%, most preferably for at least 95% in the reaction medium. Suitable examples are formic acid, acetic acid, propionic acid, butyric acid, valeric acid, caproic acid, succinic acid, glutaric acid, adipic acid, pimelic acid, suberic acid, azelaic acid, benzoic acid, isobutyric acid, isovaleric acid. Preferably acetic acid or azelaic acid is used. Relative to the substrate, the amount of the carboxylic acid is typically 10-300 wt %, preferably 20-200 wt %, most preferably 30-100 wt %.

The starting material for the preparation of azelaic acid or alkyl azelate is (E)- or (Z)-9-octadecenedioic acid or its corresponding alkylester. With the double bond located at the ninth carbon atom, 100% carbon efficiency can be reached in the conversion, since all carbon atoms that are present in the starting compound 9-octadecenedioic acid or its corresponding alkylester are turned into azelaic acid or alkyl azelate.

The starting compound (Z)-9-octadecene dioic acid can be obtained from oleic acid by enzymatic fermentation, as described for example by Ness et al. in WO2011008231. When such fermentation is carried out with an alkyl oleate, a (Z)-9-octadecenedioic acid mono-alkyl ester is obtained, as described by Dubois in WO2008104722. (Z)-9-Octadecenedioic acid dialkyl esters are conveniently obtained by simple esterification of (Z)-9-octadecene dioic acid with a suitable alkanol. Alternatively, (E)- or (Z)-9-octadecenedioic acid dialkyl esters are accessible from oleic acid via metathesis technologies, as described for example by Ngo in J. Am. Oil. Chem. Soc. 2006, 83, 629-634, or by Jiang in J. Am. Chem. Soc. 2009, 131, 16630-16631.

The azelaic acid or alkyl azelate that is obtained as the reaction product from the process according to the present invention is very advantageous as each individually can easily be converted into several other classes of chemical compounds such as for example dinitriles and diamines.

The starting compound (E)- or (Z)-9-octadecenedioic acid or its corresponding alkylester can be represented by the following formula I:

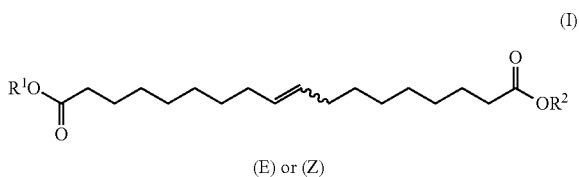

(E) or (Z)

Wherein:
$R^1$ and $R^2$ can be independently chosen and represent H or alkyl with 1-6 carbon atoms.
When both $R^1$ and $R^2$ are chosen to be H, the compound according to formula I is (E)- or (Z)-9-octadecenedioic acid. When $R^1$ and $R^2$ are chosen to be an alkyl group with 1-6 carbon atoms the compound is the dialkyl ester of 9-octadecenedioic acid. As described before $R^1$ and $R^2$ can be the same alkyl-group or they can be different from each other. When $R^1$ is chosen to be H, but $R^2$ is chosen to be an alkyl group with 1-6 carbon atoms, the compound is the monoalkyl ester of 9-octadecenedioic acid. Most preferably, $R^1$ and $R^2$ are independently chosen to represent H or an alkyl with 1-2 carbon atoms, i.e. a methyl or ethyl group.

Preferred starting compounds are 9-octadecenedioic acid or its corresponding alkylester. When starting with the preferred compound 9-octadecenedioic acid, the process according to the present invention results in the preparation of preferred azelaic acid. When starting with the preferred dialkyl esters of 9-octadecenedioic acid, the process according to the present invention results in the preparation of monoalkyl azelate, usually together with azelaic acid formed by in situ hydrolysis of ester groups in the starting compound or monoalkyl azelate product. When starting with monoalkyl esters of 9-octadecenedioic acid, the process according to the present invention results in the preparation of monoalkyl azelates together with azelaic acid. The amount of azelaic acid formed during the oxidative cleavage of dialkyl esters of 9-octadecenedioic acid depends on the ease of hydrolysis of the alkyl ester group. Especially when the ester group is the preferred methyl group, azelaic acid may be the main product instead of methyl azelate. Azelaic acid may also be essentially the sole reaction production on complete in situ hydrolysis of alkyl ester groups. Traces of dialkyl azelates may be generated by in situ esterification of monoalkyl azelates with alkanols liberated by in situ hydrolysis of ester groups in the starting compound or monoalkyl azelate product. Azelaic acid or alkyl azelate are preferred as they are easily converted into several other classes of chemical compounds such as for example dinitriles and diamines.

Conversion of a dicarboxylic acid into a dinitrile is well-known to the man skilled in the art. In general azelaic acid can be converted into azelanitrile by treatment with ammonia at higher temperatures in the presence of a suitable catalyst, as described for example by Miwa et al. in GB-797945.

Azelanitrile formed during the previous reaction can easily be converted into 1,9-nonanediamine by treatment with hydrogen in the presence of a catalyst. The hydrogenation of a dinitrile is well-known to the man skilled in the art. Reference can for example be made to JP-37000958 by Inaba et al.

Since oleic acid is available from renewable resources, production of chemicals, e.g. monomers, from oleic acid derivatives is much more eco-friendly than their production from petrochemical feedstock. This also holds for the above production route to 1,9-nonanediamine, which is an important monomer currently manufactured from petrochemical butadiene instead of renewable oleic acid, as described by Matsumoto et al. in EP-64285 and by Parshall and Ittel in "Homogeneous Catalysis", $2^{nd}$ Edition, Wiley (1992).

As described above azelaic acid or alkyl azelate as obtained in the process according to the invention is a very versatile chemical compound that can easily be converted into another chemical compound when desired. The invention therefore also relates to azelaic acid or alkyl azelate obtainable by the process according to the invention.

The process for the preparation of azelaic acid or alkyl azelate starting from 9-octadecenedioic acid or alkyl ester derivatives thereof is performed in the presence of a catalyst. Catalysts capable of effecting the oxidative cleavage of alkenes with aqueous hydrogen peroxide are well-known to the man skilled in the art. Examples can be found in the Antonelli article referred to earlier, in an article by Ruesch gen. Klaas et al. in Fat Sci. Technol. 1995, 97, 359-367, or in US-20100210873 by Kon et al. Preferably, the catalyst is based on tungsten, such as $H_2WO_4$, $Na_2WO_4$, or polytungstate species. Most preferably, the catalyst is composed of $H_2WO_4$ or $Na_2WO_4$. In a particularly preferred embodiment, $H_2WO_4$ or $Na_2WO_4$ is used in combination with a phosphate cocatalyst, e.g. in the form of phosphoric acid. In the most preferred embodiment, $H_2WO_4$ or $Na_2WO_4$ is used in combination with a phosphate cocatalyst, e.g. in the form of phosphoric acid, and an onium-type phase transfer catalyst, e.g. methyltrioctyl-ammonium chloride or 1-hexadecyl-pyridinium chloride. Using this most preferred embodiment is particularly advantageous compared to the procedure described by Antonelli et al. based on using isolated, industrially non-feasible onium tetrakis-(oxodiperoxotungsto)-phosphate as the catalyst. The amount of the metal catalyst depends on the type of catalyst that is used. The amount can easily, without undue burden be determined by the person skilled in the art. Relative to the substrate on a "per metal atom" basis, the amount of catalyst is typically 0.1-20 mol %, preferably 0.2-10 mol %, most preferably 0.5-5 mol %.

9-Octadecenedioic acid or its corresponding alkylester is cleaved into azelaic acid or alkyl azelate by the action of hydrogen peroxide. The hydrogen peroxide is used in the form of an aqueous solution, typically 3-90 wt %, preferably 20-85 wt %, most preferably 30-70 wt %. Relative to the substrate, the amount of hydrogen peroxide is typically 4-20 molar equivalents, preferably 4.2-15 molar equivalents, most preferably 4.4-12 molar equivalents. When desired, the aqueous layer containing non-converted hydrogen peroxide can be recycled for effecting additional oxidative cleavage of the substrate.

The reaction is carried out at elevated temperature, typically at 50-125° C., preferably 70-100° C., most preferably 80-90° C. The reaction may be carried out in the presence of a small amount of an organic solvent, e.g. aromatic or aliphatic solvents, but preferably no organic solvent is used. Efficient mixing is essential during the reaction.

The azelaic acid or alkyl azelate obtainable by the process according to the invention or a monomer derived from any of them can be used for the preparation of a polymer. Examples of monomers derived from azelaic acid or alkyl azelate are described above and are for example the corresponding dinitrile or corresponding diamine.

Polymers that can be produced with these compounds as monomer are for example polyesters, polyurethanes or polyesteramides. When the azelaic acid or alkyl azelate obtained by the process according to the invention is converted into a di-nitrile or a di-amine, polymers based on these types of monomers are for example polyurethanes or polyamides. The invention therefore also relates to the use of azelaic acid or alkyl azelate obtainable by the process according to the invention or monomers derived from azelaic acid or alkyl azelate for the preparation of a polymer, preferably a polyamide.

The invention will further be elucidated in the following examples, without being limited to them.

EXAMPLES

Example 1

Oxidative Cleavage of (E)-Dimethyl 9-Octadecenedioate with Added Azelaic Acid

Tungstic acid (0.0188 g) was dissolved at 60° C. in a mixture of aqueous phosphoric acid (1.50 mL of a stock solution containing 1.4443 g 85% $H_3PO_4$ per liter) and aqueous 70% hydrogen peroxide (1.60 mL). A test tube was charged with methyltrioctylammonium chloride (0.0081 g), (E)-dimethyl 9-octadecenedioate (0.4261 g), and azelaic acid (0.4709 g). The test tube, equipped with a stirring bar and a punctured septum, was placed in an oil bath of 85° C. and stirred. This led to the formation of a turbid liquid. To the test tube was added 1.10 mL of the tungstic acid in hydrogen peroxide solution (cooled to room temperature). The mixture was stirred at maximum speed overnight at 85° C. To the reaction mixture was added $CDCl_3$ (10 mL), and the $CDCl_3$ layer was analyzed by proton NMR. This showed essentially quantitative formation of a mixture of methyl azelate and azelaic acid. Work up of the $CDCl_3$ solution by drying over $Na_2SO_4$ and evaporation afforded a white powder (0.98 g), which according to proton and carbon NMR in $CD_3OD$ consisted of a mixture of methyl azelate and azelaic acid with only trace amounts of impurities.

Comparative Experiment A:
Oxidative Cleavage of (E)-Dimethyl 9-Octadecenedioate without Added Azelaic Acid Tungstic acid (0.0063 g) was dissolved at 60° C. in a mixture of aqueous phosphoric acid (0.50 mL of a stock solution containing 1.4443 g 85% $H_3PO_4$ per liter) and aqueous 70% hydrogen peroxide (0.52 mL). A test tube was charged with methyltrioctylammonium chloride (0.0078 g) and (E)-dimethyl 9-octadecenedioate (0.8616 g). The test tube, equipped with a stirring bar and a punctured septum, was placed in an oil bath of 85° C. and stirred. This led to the formation of a clear liquid. To the test tube was added the tungstic acid in hydrogen peroxide solution (cooled to room temperature). The mixture was stirred at maximum speed overnight at 85° C. To the reaction mixture was added $CDCl_3$ (10 mL), and the $CDCl_3$ layer was analyzed by proton NMR. This showed essentially quantitative formation of the epoxide derived from (E)-dimethyl 9-octadecenedioate, i.e. dimethyl 8,8'-(oxirane-2,3-diyl)dioctanoate.

Example 2

Oxidative Cleavage of (E)-Dimethyl 9-Octadecenedioate with Added Acetic Acid

Tungstic acid (0.0188 g) was dissolved at 60° C. in a mixture of aqueous phosphoric acid (1.50 mL of a stock solution containing 1.4443 g 85% $H_3PO_4$ per liter) and aqueous 70% hydrogen peroxide (1.60 mL). A test tube was charged with methyltrioctylammonium chloride (0.0081 g), (E)-dimethyl 9-octadecenedioate (0.4271 g), and acetic acid (0.3015 g). The test tube, equipped with a stirring bar and a punctured septum, was placed in an oil bath of 85° C. and stirred. This led to the formation of a liquid. To the test tube was added 1.10 mL of the tungstic acid in hydrogen peroxide solution (cooled to room temperature). The mixture was stirred at maximum speed overnight at 85° C. To the reaction mixture was added $CD_3OD$ (5 mL), and the solution was analyzed by proton NMR. This showed high yield formation of a mixture of methyl azelate and azelaic acid. Work up by addition of $CH_2Cl_2$ (100 mL), drying over $Na_2SO_4$ and evaporation afforded a white powder (0.50 g), which according to proton and carbon NMR in DMSO-$d_6$ consisted of a mixture of methyl azelate and azelaic acid with traces of impurities.

Example 3

Oxidative Cleavage of (E)-9-Octadecenedioic Acid with Added Azelaic Acid

Tungstic acid (0.0188 g) was dissolved at 60° C. in a mixture of aqueous phosphoric acid (1.50 mL of a stock solution containing 1.4443 g 85% $H_3PO_4$ per liter) and aqueous 70% hydrogen peroxide (1.60 mL). A test tube was charged with methyltrioctylammonium chloride (0.0078 g), (E)-9-octadecenedioic acid (0.3909 g), and azelaic acid (0.4736 g). The test tube, equipped with a stirring bar and a punctured septum, was placed in an oil bath of 85° C. and stirred. This led to the formation of a turbid liquid. To the test tube was added 1.10 mL of the tungstic acid in hydrogen peroxide solution (cooled to room temperature). The mixture was stirred at maximum speed overnight at 85° C. To the reaction mixture was added $CDCl_3$ (10 mL), and the $CDCl_3$ layer was analyzed by proton NMR. This showed high yield formation of a mixture of methyl azelate and azelaic acid.

Comparative Experiment B:
Oxidative Cleavage of (E)-9-Octadecenedioic Acid without Added Azelaic Acid Tungstic acid (0.0063 g) was dissolved at 60° C. in a mixture of aqueous phosphoric acid (0.50 mL of a stock solution containing 1.4443 g 85% $H_3PO_4$ per liter) and aqueous 70% hydrogen peroxide (1.04 mL). A test tube was charged with methyltrioctylammonium chloride (0.0079 g) and (E)-9-octadecenedioic acid (0.7817 g). The test tube, equipped with a stirring bar and a punctured septum, was placed in an oil bath of 85° C. To the test tube was added the tungstic acid in hydrogen peroxide solution (cooled to room temperature). This led to the formation of thick slurry that was very difficult to stir. The mixture was heated to 95° C., at which temperature efficient stirring was possible. The mixture was stirred at maximum speed overnight at 95° C. To the reaction mixture was added $CDCl_3$ (15 mL), and the $CDCl_3$ layer was analyzed by proton NMR. This showed incomplete conversion with partial formation of a mixture of methyl azelate and azelaic acid, together with large amounts of impurities. Work up of the $CDCl_3$ solution by drying over $Na_2SO_4$ and evaporation afforded a yellow oil, which according to proton NMR in $CDCl_3$ consisted of a mixture of methyl azelate and azelaic acid with large amounts of impurities.

The invention claimed is:

1. A process for the preparation of azelaic acid or alkyl azelate starting from mono-unsaturated 9-octadecenedioic acid or its corresponding alkylester, wherein the process comprises reacting 9-octadecenedioic acid or its corresponding alkylester in a reaction medium with aqueous hydrogen peroxide in the presence of 10-300 wt. %, based weight % of the 9-octadecanedioic acid, of an organic carboxylic acid other than 9-octadecene dioic acid and a tungsten-based catalyst to effect cleavage of the double bond in 9-octadecenedioic acid or the corresponding alkylester.

2. The process according to claim 1, wherein the alkyl groups in the alkyl azelate are independently chosen to contain 1 to 6 carbon atoms.

3. The process according to claim 1, wherein the organic carboxylic acid other than 9-octadecene dioic acid is a mono- or dicarboxylic acid with 1-12 carbon atoms.

4. The process according to claim 1, wherein the organic carboxylic acid other than 9-octadecene dioic acid is at least 80% soluble in the reaction medium.

5. The process according to claim 3, wherein the organic carboxylic acid other than 9-octadecene dioic acid is acetic acid or azelaic acid.

6. Azelaic acid obtained by the process according to claim 1.

7. Alkyl azelate obtained by the process according to claim 1.

8. A monomer or polymer derived from the alkyl azelate of claim 7.

9. A method for preparing a polyamide comprising reacting the alkyl azelate according to claim 7, under polyamide formation conditions.

* * * * *